United States Patent
Picard et al.

(10) Patent No.: US 7,223,883 B2
(45) Date of Patent: *May 29, 2007

(54) REMOVAL OF PERMANGANATE REDUCING COMPOUNDS FROM METHANOL CARBONYLATION PROCESS STREAM

(75) Inventors: Wayne D. Picard, Houston, TX (US); Jose J. Arturo Talancon, Mexico City (MX); David A. Trueba, Webster, TX (US); Mark O. Scates, Houston, TX (US); Raymond J. Zinobile, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 454 days.

This patent is subject to a terminal disclaimer.

(21) Appl. No.: 10/708,421

(22) Filed: Mar. 2, 2004

(65) Prior Publication Data

US 2005/0197509 A1 Sep. 8, 2005

(51) Int. Cl.
C07C 51/10 (2006.01)
C07C 51/42 (2006.01)
C07C 45/78 (2006.01)
(52) U.S. Cl. .................... 562/517; 562/608; 568/492
(58) Field of Classification Search ............ 562/517, 562/518, 519, 607, 608; 568/492
See application file for complete search history.

(56) References Cited

U.S. PATENT DOCUMENTS

| | | | |
|---|---|---|---|
| 3,769,329 A | 10/1973 | Paulik et al. | 260/488 |
| 5,001,259 A | 3/1991 | Smith et al. | 562/519 |
| 5,026,908 A | 6/1991 | Smith et al. | 562/519 |
| 5,144,068 A | 9/1992 | Smith et al. | 562/519 |
| 5,371,286 A * | 12/1994 | Blay et al. | 562/519 |
| 5,416,237 A | 5/1995 | Aubigne et al. | 562/519 |
| 5,625,095 A | 4/1997 | Miura et al. | 562/519 |
| 5,723,660 A | 3/1998 | Morimoto et al. | 562/519 |
| 5,756,836 A | 5/1998 | Shimizu et al. | 562/519 |
| 5,783,731 A | 7/1998 | Fisher et al. | 562/519 |
| 6,143,930 A * | 11/2000 | Singh et al. | 562/608 |
| 6,339,171 B1 | 1/2002 | Singh et al. | 562/519 |

FOREIGN PATENT DOCUMENTS

EP 0 161 874 11/1985

(Continued)

OTHER PUBLICATIONS

Derrick J. Watson, *The Cativa Process for the Production of Acetic Acid*, in Catalysis of Organic Reactions, vol. 75, pp. 369-380 (1998).

(Continued)

*Primary Examiner*—Karl Puttlitz
(74) *Attorney, Agent, or Firm*—Howrey LLP (57) ABSTRACT

An improvement of the methanol carbonylation process for manufacturing acetic acid is disclosed. Specifically disclosed is a method for removing permanganate reducing compounds ("PRC's") from the condensed light ends overhead stream, including (a) distilling at least a portion of the condensed light ends overhead to yield a PRC enriched second overhead stream; (b) extracting the second overhead stream with water and separating therefrom an aqueous stream containing PRC's; and (c) returning at least a portion of the extracted second overhead to the second distiller.

36 Claims, 2 Drawing Sheets

FOREIGN PATENT DOCUMENTS

| | | |
|---|---|---|
| EP | 0 487 284 | 5/1992 |
| EP | 0 687 662 | 12/1995 |
| JP | 9-40590 | 2/1997 |
| WO | 199817619 * | 4/1998 |

OTHER PUBLICATIONS

R.T. Eby & T.C. Singleton, *Methanol Carbonylation to Acetic Acid, in* Applied Industrial Catalysis, vol. 1, pp. 275-296 (1983).

* cited by examiner

REMOVAL OF PERMANGANATE REDUCING COMPOUNDS FROM METHANOL CARBONYLATION PROCESS STREAM

BACKGROUND OF INVENTION

1. Field of the Invention

This invention relates to an improved process for the removal of permanganate reducing compounds and alkyl iodides formed by the carbonylation of methanol in the presence of a Group VIII metal carbonylation catalyst. More specifically, this invention relates to an improved process for reducing and/or removing precursors of permanganate reducing compounds and alkyl iodides from intermediate streams during the formation of acetic acid by said carbonylation processes.

2. Technical Background

Among currently employed processes for synthesizing acetic acid, one of the most useful commercially is the catalyzed carbonylation of methanol with carbon monoxide as taught in U.S. Pat. No. 3,769,329 issued to Paulik et al on Oct. 30, 1973. The carbonylation catalyst comprises rhodium, either dissolved or otherwise dispersed in a liquid reaction medium or supported on an inert solid, along with a halogen-containing catalyst promoter as exemplified by methyl iodide. The rhodium can be introduced into the reaction system in any of many forms, and the exact nature of the rhodium moiety within the active catalyst complex is uncertain. Likewise, the nature of the halide promoter is not critical. The patentees disclose a very large number of suitable promoters, most of which are organic iodides. Most typically and usefully, the reaction is conducted by continuously bubbling carbon monoxide gas through a liquid reaction medium in which the catalyst is dissolved.

An improvement in the prior art process for the carbonylation of an alcohol to produce the carboxylic acid having one carbon atom more than the alcohol in the presence of a rhodium catalyst is disclosed in commonly assigned U.S. Pat. No. 5,001,259, issued Mar. 19, 1991; U.S. Pat. No. 5,026,908, issued Jun. 25, 1991; and U.S. Pat. No. 5,144,068, issued Sep. 1, 1992; and European Patent No. EP 0 161 874 B2, published Jul. 1, 1992. As disclosed therein, acetic acid is produced from methanol in a reaction medium containing methyl acetate, methyl halide, especially methyl iodide, and rhodium present in a catalytically effective concentration. These patents disclose that catalyst stability and the productivity of the carbonylation reactor can be maintained at surprisingly high levels, even at very low water concentrations, i.e. 4 weight percent or less, in the reaction medium (despite the general industrial practice of maintaining approximately 14–15 wt % water) by maintaining in the reaction medium, along with a catalytically effective amount of rhodium and at least a finite concentration of water, a specified concentration of iodide ions over and above the iodide content which is present as methyl iodide or other organic iodide. The iodide ion is present as a simple salt, with lithium iodide being preferred. The patents teach that the concentration of methyl acetate and iodide salts are significant parameters in affecting the rate of carbonylation of methanol to produce acetic acid, especially at low reactor water concentrations. By using relatively high concentrations of the methyl acetate and iodide salt, one obtains a surprising degree of catalyst stability and reactor productivity even when the liquid reaction medium contains water in concentrations as low as about 0.1 wt %, so low that it can broadly be defined simply as "a finite concentration" of water. Furthermore, the reaction medium employed improves the stability of the rhodium catalyst, i.e. resistance to catalyst precipitation, especially during the product recovery steps of the process. In these steps, distillation for the purpose of recovering the acetic acid product tends to remove from the catalyst the carbon monoxide which in the environment maintained in the reaction vessel, is a ligand with stabilizing effect on the rhodium. U.S. Pat. Nos. 5,001,259, 5,026,908 and 5,144,068 are herein incorporated by reference.

It has been found that although a low water carbonylation process for producing acetic acid reduces such by-products as carbon dioxide, hydrogen, and propionic acid, the amount of other impurities, present generally in trace amounts, is also increased, and the quality of acetic acid sometimes suffers when attempts are made to increase the production rate by improving catalysts, or modifying reaction conditions.

These trace impurities affect quality of acetic acid, especially when they are recirculated through the reaction process. The impurities that decrease the permanganate time of the acetic acid include carbonyl compounds and unsaturated carbonyl compounds. As used herein, the phrase "carbonyl" is intended to mean compounds that contain aldehyde or ketone functional groups, which compounds may or may not possess unsaturation. See *Catalysis of Organic Reaction*, 75, 369–380 (1998), for further discussion on impurities in a carbonylation process.

The present invention is directed to reducing and/or removing permanganate reducing compounds (PRC"s) such as acetaldehyde, acetone, methyl ethyl ketone, butyraldehyde, crotonaldehyde, 2-ethyl crotonaldehyde, and 2-ethyl butyraldehyde and the like, and the aldol condensation products thereof. The present invention also leads to reduction of propionic acid.

The carbonyl impurities described above, such as acetaldehyde, may react with iodide catalyst promoters to form multi-carbon alkyl iodides, e.g., ethyl iodide, propyl iodide, butyl iodide, pentyl iodide, hexyl iodide and the like. It is desirable to remove alkyl iodides from the reaction product because even small amounts of these impurities in the acetic acid product tend to poison the catalyst used in the production of vinyl acetate, the product most commonly produced from acetic acid. The present invention is thus also directed to removal of alkyl iodides, in particular $C_{2-12}$ alkyl iodide compounds. Accordingly, because many impurities originate with acetaldehyde, it is a primary objective to remove or reduce the acetaldehyde and alkyl iodide content in the process.

Conventional techniques to remove impurities include treating the acetic acid product with oxidizers, ozone, water, methanol, activated-carbon, amines, and the like, which treatment may or may not be combined with distillation of the acetic acid. The most typical purification treatment involves a series of distillations of the final product. It is known, for example, from U.S. Pat. No. 5,783,731 to remove carbonyl impurities from organic streams by treating the organic streams with an amine compound such as hydroxylamine, which reacts with the carbonyl compounds to form oximes, followed by distillation to separate the purified organic product from the oxime reaction products. However, the additional treatment of the final product adds cost to the process, and distillation of the treated acetic acid product can result in additional impurities being formed.

While it is possible to obtain acetic acid of relatively high purity, the acetic acid product formed by the low-water carbonylation process and purification treatment described above frequently remains somewhat deficient with respect to the permanganate time due to the presence of small proportions of residual impurities. Since a sufficient permanganate time is an important commercial test, which the acid product must meet to be suitable for many uses, the presence of impurities that decrease permanganate time is objectionable. Moreover, it is not economically or commercially feasible to remove minute quantities of these impurities from the acetic acid by distillation because some of the impurities have boiling points close to that of the acetic acid product.

It has thus become important to identify economically viable methods of removing impurities elsewhere in the carbonylation process without contaminating the final product or adding unnecessary costs. U.S. Pat. No. 5,756,836, incorporated herein by reference, discloses a method for manufacturing high purity acetic acid by adjusting the acetaldehyde concentration of the reaction solution below 1500 ppm. It is stated that by maintaining the acetaldehyde concentration below this threshold, it is possible to suppress the formation of impurities such that one need only distill the crude acetic acid product to obtain high purity acetic acid.

European Patent No. EP 0 487 284 B1, published Apr. 12, 1995, discloses that carbonyl impurities present in the acetic acid product generally concentrate in the overhead from the light ends column. Accordingly, the light ends column overhead is treated with an amine compound (such as hydroxylamine), which reacts with the carbonyl compounds to form oxime derivatives that can be separated from the remaining overhead by distillation, resulting in an acetic acid product with improved permanganate time.

European Patent Application No. EP 0 687 662 A2 and U.S. Pat. No. 5,625,095, incorporated herein by reference, describe a process for producing high purity acetic acid in which an acetaldehyde concentration of 400 ppm or less is maintained in the reactor by using a single or multistage distillation process to remove acetaldehyde. Streams suggested for processing to remove acetaldehyde include a light phase containing primarily water, acetic acid and methyl acetate; a heavy phase containing primarily methyl iodide, methyl acetate and acetic acid; an overhead stream containing primarily methyl iodide and methyl acetate; or a recirculating stream formed by combining the light and heavy phase. These references do not identify which of these streams possesses the greatest concentration of acetaldehyde.

EP 0 687 662 A2 and U.S. Pat. No. 5,625,095 also disclose management of reaction conditions to control the formation of acetaldehyde in the reactor. Although it is stated that formation of by-products such as crotonaldehyde, 2-ethylcrotonaldehyde, and alkyl iodides is reduced by controlling the formation of acetaldehyde, it is also pointed out that management of reaction conditions as proposed increases the formation of propionic acid, an undesirable by-product.

More recently, it has been disclosed in commonly assigned U.S. Pat. Nos. 6,143,930 and 6,339,171 that it is possible to significantly reduce the undesirable impurities in the acetic acid product by performing a multi-stage purification on the light ends column overhead. These patents disclose a purification process in which the light ends overhead is distilled twice, in each case taking the acetaldehyde overhead and returning a methyl iodide rich residuum to the reactor. The acetaldehyde-rich distillate is extracted with water to remove the majority of the acetaldehyde for disposal, leaving a significantly lower acetaldehyde concentration in the raffinate that is recycled to the reactor. U.S. Pat. Nos. 6,143,930 and 6,339,171 are incorporated herein by reference.

While the above-described processes have been successful in removing carbonyl impurities from the carbonylation system and for the most part controlling acetaldehyde levels and permanganate time problems in the final acetic acid product, further improvements can still be made. Accordingly, there remains a need for alternative processes to improve the efficiency of acetaldehyde removal. The present invention provides one such alternative solution.

SUMMARY OF INVENTION

In one aspect, the present invention provides a process for producing acetic acid that includes the following steps: (a) reacting methanol and carbon dioxide in a suitable reaction medium that includes a catalyst and an organic iodide; (b) separating the products of the reaction into a volatile product phase that contains acetic acid, organic iodide, and at least one permanganate reducing compound (PRC), and a less volatile phase containing the catalyst and acetic acid;(c) distilling the volatile product phase to yield a purified product and a first overhead that contains organic iodide, water, acetic acid, and unreacted methanol; (d) distilling at least a portion of the first overhead to produce a PRC enriched second overhead; (e) extracting the second overhead with water and separating therefrom an aqueous extract containing concentrated PRC's for disposal; and(f) distilling at least a portion of the extracted second overhead together with the first overhead portion.

Preferably, another portion of the extracted second overhead is recycled to the reactor.

In another aspect, the present invention provides an improved method for separating a mixture containing water, acetic acid, methyl iodide, methyl acetate, methanol, at least one $C_{2-12}$ alkyl iodide and at least one permanganate reducing compound (PRC). The improved method includes the following steps: (a) distilling the mixture to form a PRC enriched overhead stream; (b) extracting the PRC enriched overhead stream with water and separating therefrom an aqueous stream containing at least one PRC; and (c) distilling at least a portion of the extracted PRC enriched overhead together with the mixture.

In still another aspect, the present invention provides an improved method for reduction and/or removal of permanganate-reducing compounds (PRC's) and $C_{2-12}$ alkyl iodide compounds formed in the carbonylation of methanol to a product of acetic acid. In the improved method, the methanol is carbonylated in a reaction medium containing a catalyst, and an organic iodide; the products of the carbonylation reaction are separated into (1) a volatile phase containing acetic acid product, organic iodide, water, and at least one PRC, and (2) a less volatile phase containing the catalyst; the volatile phase is distilled to yield a purified product and a first overhead containing organic iodide, water, acetic acid, and PRC. The improvement includes the steps of (a) distilling the first overhead to form a PRC enriched second overhead stream; (b) extracting the second overhead stream with water and separating therefrom an aqueous stream containing PRC's; and (c) distilling at least a portion of the extracted second overhead together with the first overhead.

In particularly preferred embodiments of the invention, the second overhead or PRC enriched overhead contains dimethyl ether in an amount effective to reduce the solubility of methyl iodide in the aqueous extract stream.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is intended to cover all modifications, equivalents and alternatives falling within the scope of the invention as defined by the appended claims.

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers" specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The purification process of the present invention is useful in any process used to carbonylate methanol (or another carbonylatable reactant such as methyl acetate, methyl formate, or dimethyl ether) to acetic acid in the presence of a Group VIII metal catalyst such as rhodium and an iodide promoter. A particularly useful process is the low water rhodium-catalyzed carbonylation of methanol to acetic acid as exemplified in U.S. Pat. No. 5,001,259. Generally, the rhodium component of the catalyst system is believed to be present in the form of a coordination compound of rhodium with a halogen component providing at least one of the ligands of such coordination compound. In addition to the coordination of rhodium and halogen, it is also believed that carbon monoxide coordinates with rhodium. The rhodium component of the catalyst system may be provided by introducing into the reaction zone rhodium in the form of rhodium metal, rhodium salts such as the oxides, acetates, iodides, etc., or other coordination compounds of rhodium, and the like.

The halogen-promoting component of the catalyst system consists of a halogen compound comprising an organic halide. Thus, alkyl, aryl, and substituted alkyl or aryl halides can be used. Preferably, the halide promoter is present in the form of an alkyl halide in which the alkyl radical corresponds to the alkyl radical of the feed alcohol, which is carbonylated. Thus, in the carbonylation of methanol to acetic acid, the halide promoter will contain methyl halide, and more preferably methyl iodide.

The liquid reaction medium employed may include any solvent compatible with the catalyst system and may include pure alcohols, or mixtures of the alcohol feedstock and/or the desired carboxylic acid and/or esters of these two compounds. The preferred solvent and liquid reaction medium for the low water carbonylation process is the carboxylic acid product. Thus, in the carbonylation of methanol to acetic acid, the preferred solvent is acetic acid.

Water is contained in the reaction medium but at concentrations well below that which has heretofore been thought practical for achieving sufficient reaction rates. It has previously been taught that in rhodium-catalyzed carbonylation reactions of the type set forth in this invention, the addition of water exerts a beneficial effect upon the reaction rate (U.S. Pat. No. 3,769,329). Thus most commercial operations run at water concentrations of at least about 14 wt %. Accordingly, it is quite unexpected that reaction rates substantially equal to and above reaction rates obtained with such high levels of water concentration can be achieved with water concentrations below 14 wt % and as low as about 0.1 wt %.

In accordance with the carbonylation process most useful to manufacture acetic acid according to the present invention, the desired reaction rates are obtained even at low water concentrations by including in the reaction medium methyl acetate and an additional iodide ion which is over and above the iodide which is present as a catalyst promoter such as methyl iodide or other organic iodide. The additional iodide promoter is an iodide salt, with lithium iodide being preferred. It has been found that under low water concentrations, methyl acetate and lithium iodide act as rate promoters only when relatively high concentrations of each of these components are present and that the promotion is higher when both of these components are present simultaneously (U.S. Pat. No. 5,001,259). The concentration of lithium iodide used in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

The carbonylation reaction of methanol to acetic acid product may be carried out by contacting the methanol feed, which is in the liquid phase, with gaseous carbon monoxide bubbled through a liquid acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or quaternary cation such as a quaternary amine or phosphine or inorganic cation can be used provided that the salt is sufficiently soluble in the reaction medium to provide the desired level of the iodide. When the iodide is added as a metal salt, preferably it is an iodide salt of a member of the group consisting of the metals of Group IA and Group IIA of the periodic table as set forth in the "Handbook of Chemistry and Physics" published by CRC Press, Cleveland, Ohio, 1975–76 (56th edition). In particular, alkali metal iodides are useful, with lithium iodide being preferred. In the low water carbonylation process most useful in this invention, the additional iodide over and above the organic iodide promoter is present in the catalyst solution in amounts of from about 2 to about 20 wt %, the methyl acetate is present in amounts of from about 0.5 to about 30 wt %, and the lithium iodide is present in amounts of from about 5 to about 20 wt %. The rhodium catalyst is present in amounts of from about 200 to about 2000 parts per million (ppm).

Typical reaction temperatures for carbonylation will be approximately 150 to about 250° C., with the temperature range of about 180 to about 220° C. being the preferred range. The carbon monoxide partial pressure in the reactor can vary widely but is typically about 2 to about 30 atmospheres, and preferably, about 3 to about 10 atmospheres. Because of the partial pressure of by-products and the vapor pressure of the contained liquids, the total reactor pressure will range from about 15 to about 40 atmospheres.

Figure 1:
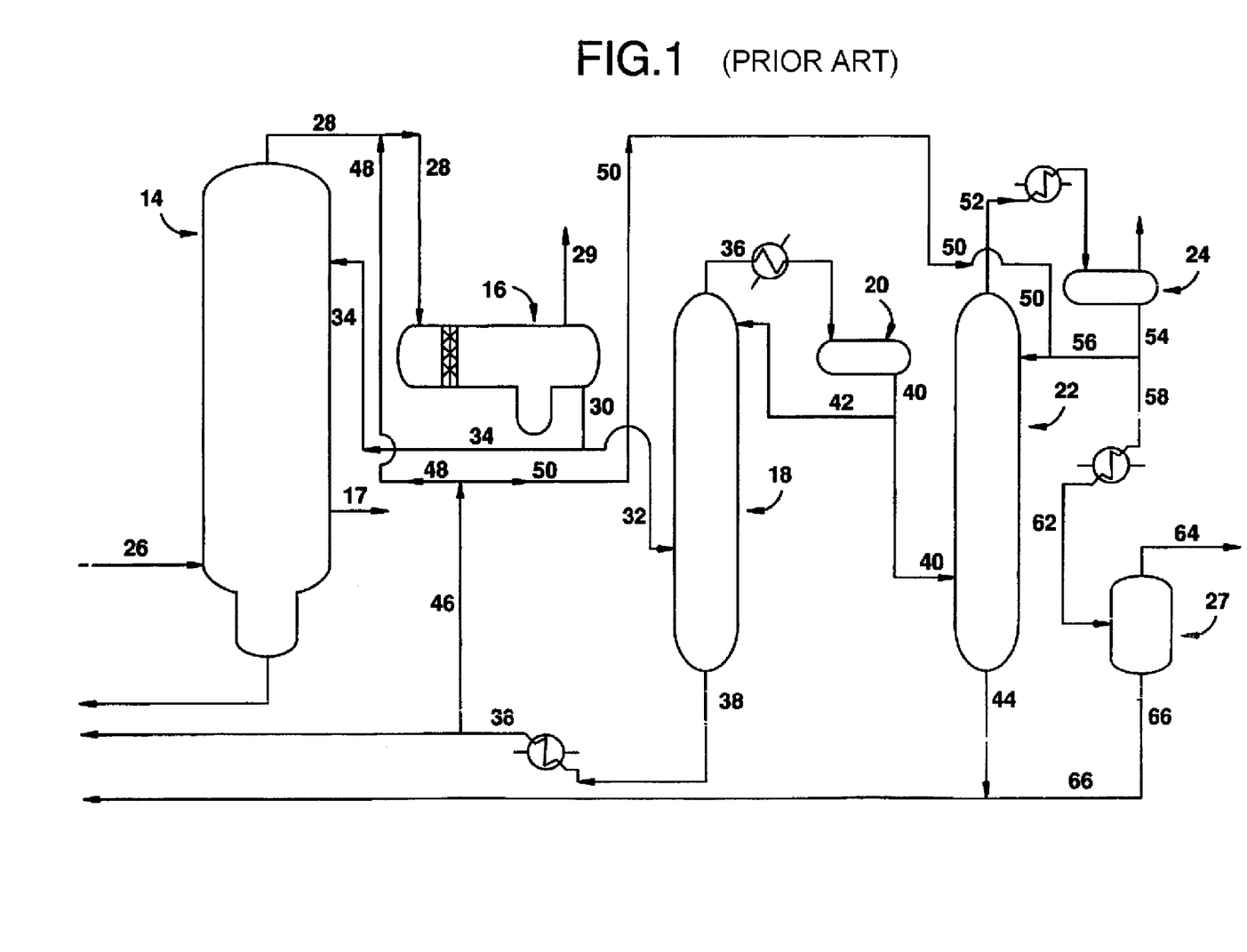
FIG. 1 illustrates the prior art process, as disclosed in U.S. Pat. No. 6,339,171, for the removal of carbonyl impurities from an intermediate stream of the carbonylation process for the production of acetic acid by a carbonylation reaction.

A typical reaction and acetic acid recovery system that is used for the iodide-promoted rhodium catalyzed carbonylation of methanol to acetic acid is shown in FIG. 1 and includes a liquid phase carbonylation reactor, flasher, and a methyl iodide acetic acid light ends column 14 which has an acetic acid side stream 17 which proceeds to further purification. The reactor and flasher are not shown in FIG. 1. These are considered standard equipment now well known in the carbonylation process art. The carbonylation reactor is typically either a stirred vessel or a bubble column reactor, within which the reacting liquid or slurry contents are maintained automatically at a constant level. Into this reactor there are continuously introduced fresh methanol, carbon monoxide, sufficient water as needed to maintain at least a finite concentration of water in the reaction medium, recycled catalyst solution from the flasher base, a recycled methyl iodide and methyl acetate phase, and a recycled aqueous acetic acid phase from an overhead receiver decanter of the methyl iodide acetic acid light ends or splitter column 14. Distillation systems are employed that provide means for recovering the crude acetic acid and recycling catalyst solution, methyl iodide, and methyl acetate to the reactor. In a preferred process, carbon monoxide is continuously introduced into the carbonylation reactor just below the agitator, which is used to stir the contents. The gaseous feed is thoroughly dispersed through the reacting liquid by this stirring means. A gaseous purge stream is vented from the reactor to prevent buildup of gaseous by-products and to maintain a set carbon monoxide partial pressure at a given total reactor pressure. The temperature of the reactor is controlled and the carbon monoxide feed is introduced at a rate sufficient to maintain the desired total reactor pressure.

Liquid product is drawn off from the carbonylation reactor at a rate sufficient to maintain a constant level therein and is introduced to the flasher. In the flasher the catalyst solution is withdrawn as a base stream (predominantly acetic acid containing the rhodium and the iodide salt along with lesser quantities of methyl acetate, methyl iodide, and water), while the vapor overhead stream of the flasher contains largely the product acetic acid along with methyl iodide, methyl acetate, and water. Dissolved gases exiting the reactor and entering the flasher consist of a portion of the carbon monoxide along with gaseous by products such as methane, hydrogen, and carbon dioxide and exit the flasher as part of the overhead stream. The overhead stream is directed to the light ends or splitter column 14 as stream 26.

It has been disclosed in U.S. Pat. Nos. 6,143,930 and 6,339,171 that there is a higher concentration, about 3 times, of the PRC's and in particular acetaldehyde content in the light phase than in the heavy phase stream exiting column 14. Thus, in accordance with the present invention, PRC-containing stream 28 is directed to an overhead receiver decanter 16 whence the light ends phase, stream 30, is directed to distillation column 18.

The present invention may broadly be considered as an improved process for distilling PRC's, primarily aldehydes and alkyl iodides, from a vapor phase acetic acid stream. The vapor phase stream is distilled and extracted to remove PRC's. An especially preferred method of removing aldehydes and alkyl iodides from a first vapor phase acetic acid stream and reducing levels of propionic acid in the acetic acid product, includes the following steps: a) condensing the first vapor phase acetic acid stream in a first condenser and biphasically separating it to form a first heavy liquid phase product and a first light liquid phase product wherein said first heavy liquid phase contains the larger proportion of catalytic components than said first light liquid phase product; b) distilling the light liquid phase product in a first distillation column to form a second vapor phase acetic acid product stream which is enriched with aldehydes and alkyl iodides with respect to said first vapor phase acetic acid stream; c) condensing the second vapor phase stream in a second condenser to form a second liquid phase product; d) distilling the second liquid phase product in a second distillation column to form a third vapor phase stream;e) condensing the third vapor phase stream and extracting the condensed stream with water to remove residual acetaldehyde therefrom; and f) recycling at least a portion of the extracted third vapor phase stream to the second distillation column.

An embodiment of the prior art as disclosed in U.S. Pat. No. 6,339,171 is shown in FIG. 1. Referring to FIG. 1, the first vapor phase acetic acid stream (28) contains methyl iodide, methyl acetate, acetaldehyde and other carbonyl components. This stream is then condensed and separated (in vessel 16) to separate the heavy phase product containing the larger proportion of catalytic components—which is recirculated to the reactor (not shown in FIG. 1), and a light phase (30) containing acetaldehyde, water, and acetic acid.

Either phase of the light ends overhead may be subsequently distilled to remove the PRC's and primarily the acetaldehyde component of the stream, although it is preferred to remove PRC's from the light phase (30) because it has been found that the concentration of acetaldehyde is somewhat greater in that phase. In the embodiment depicted and described herein, the distillation is carried out in two stages; but it will be appreciated that the distillation may be performed in a single column as well.

The light phase (30) is directed to column 18, which serves to form a second vapor phase (36) enriched in aldehydes and alkyl iodides with respect to stream 28. Steam 36 is condensed (vessel 20) and biphasically separated to form a second heavy liquid phase product and a second light phase liquid product. This second heavy liquid phase contains a higher proportion of catalytic components than the second light liquid phase and is subsequently recirculated to the reactor. The second liquid light phase (40) containing acetaldehyde, methyl iodide, methanol, and methyl acetate is directed to a second distillation column (22) wherein the acetaldehyde is separated from the other components. This inventive process has been found to reduce and/or remove at least 50% of the alkyl iodide impurities found in an acetic acid stream. It has also been shown that acetaldehyde and its derivatives is reduced and/or removed by at least 50%, most often greater than 60%. As a result, it is possible to keep the concentration of propionic acid in the acetic acid product below about 400 parts per million by weight, and preferably below 250 parts per million.

From the top of the light ends or splitter column 14, vapors are removed via stream 28, condensed, and directed to vessel 16. The vapors are chilled to a temperature sufficient to condense and separate the condensable methyl iodide, methyl acetate, acetaldehyde and other carbonyl components, and water into two phases. A portion of stream 28 contains noncondensable gases such as carbon dioxide, hydrogen, and the like and can be vented as shown in stream 29 on FIG. 1. Also leaving overhead receiver decanter 16, but not illustrated in FIG. 1, is the heavy phase of stream 28. Ordinarily this heavy phase is recirculated to the reactor, but a slip stream, generally a small amount, e.g., 25 vol. %, preferably less than about 20 vol. %, of the heavy phase may also be directed to a carbonyl treatment process and the remainder recycled to the reactor or reaction system. This slip stream of the heavy phase may be treated individually or combined with the light phase (stream 30) for further distillation and extraction of carbonyl impurities.

The light phase (stream 30) is directed to distillation column 18. A portion of stream 30 is directed back to the light ends column 14 as reflux stream 34. The remainder of stream 30 enters column 18 as stream 32 in about the middle of the column. Column 18 serves to concentrate the aldehyde components of stream 32 into overhead stream 36 by separating water and acetic acid from the lighter components. Stream 32 is distilled in first distillation column 18, which preferably contains approximately 40 trays, and temperature ranges therein from about 283° F. (139.4° C.) at the bottom to about 191° F. (88.3° C.) at the top of the column. Exiting the bottom of 18 is stream 38 containing approximately 70% water and 30% acetic acid. Stream 38 is processed, generally cooled utilizing a heat exchanger, is recycled to the light ends column overhead decanter 16 via streams 46, 48 and ultimately to the reactor or reaction system. It has been found that recycling a portion of stream 38 identified as stream 46 back through decanter 16 increases efficiency of the inventive process and allows for more acetaldehyde to be present in the light phase, stream 32. Stream 36 has been found to have approximately seven times more aldehyde content when stream 38 is recycled through decanter 16 in this manner. Exiting the top of column 18 is stream 36 containing PRC's and in particular acetaldehyde, methyl iodide, methyl acetate, and methanol, and alkyl iodides. Stream 36 is then directed to an overhead receiver 20 after it has been chilled to condense any condensable gases present.

Exiting overhead receiver 20 is stream 40 containing acetaldehyde, methyl iodide, methyl acetate, and methanol. A portion of stream 40 is returned to column 18 as reflux stream 42. The remainder of stream 40 enters second distillation column 22 close to the bottom of the column. Column 22 serves to separate the majority of the acetaldehyde from the methyl iodide, methyl acetate, and methanol in the stream 40. In one embodiment, column 22 contains about 100 trays and is operated at a temperature ranging from about 224° F. (106.6° C.) at the bottom to about 175° F. (79.4° C.) at the top. In an alternate, preferred embodiment, column 22 contains structured packing in place of trays. The preferred packing is a structured packing with an interfacial area of about 65 $ft^2/ft^3$, preferably made from a metallic alloy like 2205 or other like packing material, provided it is compatible with the compositions to be purified in the column. It was observed during experimentation that uniform column loading, which is required for good separation, was better with structured packing than with trays. Alternatively, ceramic packing may be employed. The residue of column 22, stream 44, exits at the bottom of the column and is recycled to the carbonylation process.

As disclosed in U.S. Pat. No. 6,339,171, it has been discovered that during the heating of column 22, high molecular weight polymers of acetaldehyde form. These higher molecular weight polymers (molecular weight greater than about 1000) are believed to form during processing of the light phase and are viscous and thixotropic. As heat is applied to the system, they tend to harden and adhere to the walls of the tower where their removal is cumbersome. Once polymerized, they are only slightly soluble in organic or aqueous solvents and can be removed from the system only by mechanical means. Thus an inhibitor is needed, preferably in column 22, to reduce the formation of these impurities, i.e., metaldehyde and paraldehyde and higher molecular weight polymers of acetaldehyde (AcH). Inhibitors generally consist of $C_{1-10}$ alkanols, preferably methanol; water; acetic acid and the like used individually or in combination with each other or with one or more other inhibitors. Stream 46, which is a portion of column 18 residue and a slip stream of stream 38, contains water and acetic acid and hence can serve as an inhibitor. As shown in FIG. 1, stream 46 splits to form streams 48 and 50. Stream 50 is added to column 22 to inhibit formation of metaldehyde and paraldehyde impurities and higher molecular weight polymers. Since the residue of second column 22 is recycled to the reactor, any inhibitors added must be compatible with the reaction chemistry. It has been found that small amounts of water, methanol, acetic acid, or a combination thereof, do not interfere with the reaction chemistry and practically eliminate the formation of polymers of acetaldehyde. Stream 50 is also preferably employed as an inhibitor since this material does not change the reactor water balance. Although water is not particularly preferred as an inhibitor, other important advantages are obtained by adding water to column 22 as will be explained below.

Exiting the top of column 22 is stream 52 containing PRC's. Stream 52 is directed to a condenser and then to overhead receiver 24. After condensation, any non-condensable materials are vented from receiver 24; the condensed materials exit receiver 24 as stream 54. Stream 56, a slip stream of stream 54, is used as reflux for column 22. Exiting the bottom of column 22 is stream 44 containing methyl iodide, methanol, methyl acetate, methanol and water. This stream is combined with stream 66, which will be described below, and directed to the reactor.

It is important for the extraction mechanism that the overhead stream of column 22 remain cold, generally at a temperature of about 13° C. This stream may be obtained or maintained at about 13° C. by conventional techniques known to those of skill in the art, or any mechanism generally accepted by the industry.

Upon exiting receiver 24, stream 58 is preferably sent through a condenser/chiller (now stream 62) and then to an extractor 27 to remove and recycle small amounts of methyl iodide from the aqueous PRC stream. In extractor 27, PRC's and alkyl iodides are extracted with water, preferably water from an internal stream so as to maintain water balance within the reaction system. As a result of this extraction, methyl iodide separates from the aqueous PRC's and alkyl iodide phase. In a preferred embodiment, a mixer-settler with a water-to-feed ratio of about 2 is employed.

The aqueous extract stream 64 leaves the extractor from the top thereof. This PRC-rich, and in particular, acetaldehyde-rich aqueous phase is directed to waste treatment. Also exiting the extractor is raffinate stream 66 containing methyl iodide, which is normally recycled to the reaction system and ultimately to the reactor.

The present applicants have now discovered that returning at least a portion of raffinate stream 66 to distillation column 22 improves the aldehyde removal efficiency of the entire system. This can be accomplished by returning at least a portion of stream 66 to any point between stream 32 (the feed to column 18) and extractor 27. In the embodiment shown in FIG. 2, a portion of stream 66 is split off as stream 68 and fed to column 22, either by mixing with the column feed stream 40 or by feeding stream 68 directly to the column at another point.

Figure 2:
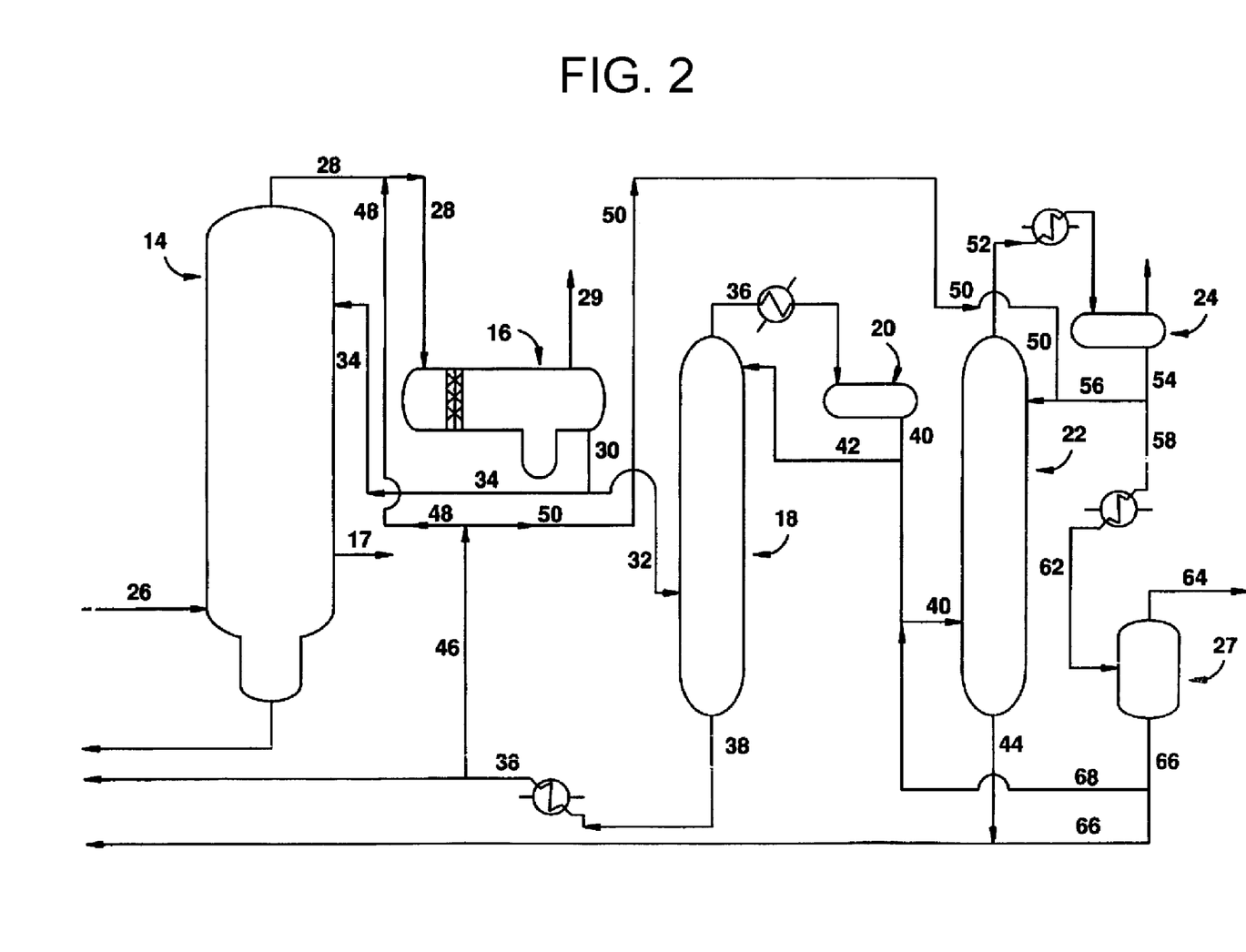
FIG. 2 illustrates a preferred embodiment of the present invention.

In one embodiment of the invention, all of stream 66 may be returned to column 22. It has been discovered, however, that it is preferable to return at least a portion of stream 66 to the reaction system rather than returning the entire stream to column 22. When the applicants began testing the present invention, it was observed that the pressure in column 22 rose significantly over time, indicating an accumulation of a volatile component in the system that was not being removed in the extraction. Applicants discovered that there were a number of chemical reactions taking place within column 22, including the hydrolysis of methyl acetate and methyl iodide to methanol and the subsequent formation of dimethyl ether (DME). DME was identified as the volatile component that was causing the increase in column pressure. When all of raffinate stream 66 from extractor 27 is recycled to column 22, the DME formed in the column is not removed from the system. It turns out, however, that the issue can be resolved by recycling a portion of stream 66 directly or indirectly to the reactor system. For example, stream 66 may be recycled to vessel 16, where it combines with the heavy phase that returns to the reactor as described above. Because DME can be carbonylated in the reactor to produce acetic acid, recycling some of the DME-containing stream 66 directly or indirectly to the reactor effectively prevents DME from accumulating in the acetaldehyde removal system.

At the same time, however, the present applicants have also discovered an unexpected advantage to the presence of small amounts of DME in the acetaldehyde removal system. Specifically, it turns out that DME reduces the solubility of methyl iodide in water. Thus the presence of DME in the feed to extractor 27 reduces the amount of methyl iodide extracted into stream 64 and lost in wastewater treatment. By way of example, the applicants observed that the concentration of methyl iodide in stream 64 dropped from about 1.8% when no DME was present to about 0.5% when DME was present. As explained hereinabove, because methyl iodide is an especially costly component of the reaction system it is highly desirable to minimize the amount of methyl iodide that is removed from the process as waste so as to reduce the quantity of fresh methyl iodide that must be fed to the reactor. Accordingly, a further aspect of the present invention includes the step of injecting additional DME upstream of extractor 27, for example into stream 62, to reduce the loss of methyl iodide into the aqueous extract stream 64. Alternatively, it is possible to generate additional DME within the process by feeding additional water to column 22 in either feed stream 40 or reflux stream 56.

While the invention has been described with reference to the preferred embodiments, obvious modifications and alterations are possible by those skilled in the related art. In particular, although the present invention has been generally described above utilizing the light ends phase of column 14, any stream in the carbonylation process having a high concentration of PRC's and alkyl iodides may be treated in accordance with the present invention. Therefore, it is intended that the invention include all such modifications and alterations to the full extent that they come within the scope of the following claims or the equivalents thereof.

The invention claimed is:

1. A process for reduction and/ or removal of permanganate-reducing compounds (PRC's) and $C_{2-12}$ alkyl iodide compounds formed in the carbonylation of a carbonylatable reactant selected from the group consisting of methanol, methyl acetate, methyl formate and dimethyl ether and mixtures thereof to produce a product comprising acetic acid, comprising the steps of:
   separating said carbonylation product to provide a volatile phase comprising acetic acid, and a less volatile phase;
   distilling said volatile phase to yield a purified acetic acid product and a first overhead comprising organic iodide, water, acetic acid, and at least one PRC;
   distilling at least a portion of the first overhead in a distillation apparatus to form a PRC enriched second overhead;
   extracting the second overhead with water and separating therefrom an aqueous stream comprising said at least one PRC; and
   recycling at least a first portion of the extracted second overhead to said distillation apparatus.

2. The process of claim 1, further comprising introducing at least a second portion of the extracted second overhead directly or indirectly into the reaction medium.

3. The process of claim 2, wherein said second overhead comprises dimethyl ether in an amount effective to reduce the solubility of methyl iodide in said aqueous stream.

4. The process of claim 2, further comprising the step of adding dimethyl ether to the second overhead.

5. The process of claim 2, further comprising forming dimethyl ether in said distillation apparatus.

6. The process of claim 5, further comprising the step of adding water to a stream associated with said distillation apparatus, whereby dimethyl ether is formed in the distillation apparatus.

7. The process of claim 1, wherein the recycled first portion of the extracted second overhead is fed to the distillation apparatus together with the first overhead portion.

8. The process of claim 1, wherein the recycled first portion of the extracted second overhead is fed to the distillation apparatus separately from the first overhead portion.

9. The process of claim 1, further comprising the step of adding dimethyl ether into at least one stream selected from the group consisting of said volatile phase, said first overhead, said second overhead, a reflux stream associated with the distillation of said volatile phase, and a reflux stream of said distillation apparatus.

10. The process of claim 1, wherein said at least one PRC comprises acetaldehyde.

11. The process of claim 10, wherein a sufficient quantity of said acetaldehyde is removed from said volatile phase to maintain a concentration of less than about 400 parts per million by weight of propionic acid in said purified acetic acid product.

12. The process of claim 10, wherein a sufficient quantity of said acetaldehyde is removed from said volatile phase to maintain a concentration of less than about 250 parts per million by weight of propionic acid in said purified acetic acid product.

13. The process of claim 1, wherein the step of distilling said first overhead comprises a plurality of consecutive distillation steps, and wherein the first portion of said extracted second overhead is recycled to a stream associated with the second or later step of said distillation steps.

14. A process for producing acetic acid, comprising the steps of:
   (a) carbonylating at least one reactant selected from the group consisting of methanol, methyl acetate, methyl formate and dimethyl ether in a reactor containing a suitable reaction medium;

(b) separating the products of said carbonylation into a volatile product phase comprising acetic acid and at least one permanganate reducing compound (PRC), and a less volatile phase;

(c) distilling said volatile product phase to yield a purified acetic acid product and a first overhead comprising organic iodide, water, acetic acid, and said at least one PRC;

(d) distilling at least a portion of the first overhead to produce a PRC-enriched second overhead; and (e) extracting the second overhead with water and separating therefrom an aqueous extract containing concentrated PRC's for disposal, wherein at least a first portion of the extracted second overhead is recycled and distilled in step (d) with the first overhead.

15. The process of claim 14, wherein said second overhead comprises dimethyl ether in an amount effective to reduce the solubility of methyl iodide in said aqueous stream.

16. The process of claim 14, further comprising the step of adding dimethyl ether to at least one stream selected from the group consisting of said volatile phase, said first overhead, said second overhead, a reflux stream associated with the distillation of the volatile phase, and a stream associated with the distillation of the first overhead portion.

17. The process of claim 14, further comprising recycling at least a second portion of the extracted second overhead directly or indirectly to the reactor.

18. The process of claim 17, further comprising forming dimethyl ether during the distillation of the first overhead portion and reacting at least a portion of the dimethyl ether with carbon monoxide in the reactor.

19. The process of claim 18, further comprising the step of injecting water into the first overhead or into the first portion of the extracted second overhead to promote formation of dimethyl ether during the distillation of the first overhead portion.

20. The process of claim 14, wherein the step of distilling at least a portion of the first overhead comprises a plurality of consecutive distillation steps, and wherein the first portion of said extracted second overhead is recycled to a stream associated with the second or later step of said distillation steps.

21. The process of claim 14, wherein said at least one PRC comprises acetaldehyde.

22. The process of claim 21, wherein a sufficient quantity of said acetaldehyde is removed from said volatile phase to maintain a concentration of less than about 400 parts per million by weight of propionic acid in said purified acetic acid product.

23. The process of claim 21, wherein a sufficient quantity of said acetaldehyde is removed from said volatile phase to maintain a concentration of less than about 250 parts per million by weight of propionic acid in said purified acetic acid product.

24. A process for separating a mixture containing water, acetic acid, methyl iodide, methyl acetate, methanol, at least one $C_{2-12}$ alkyl iodide and at least one permanganate reducing compound (PRC), comprising:

(a) distilling the mixture to provide a PRC enriched overhead stream comprising methyl iodide, water and said at least one PRC;

(b) extracting the PRC enriched overhead stream with water and separating therefrom an aqueous stream containing said at least one PRC; and (c) distilling at least a first portion of the extracted PRC enriched overhead with the mixture.

25. The process of claim 24, wherein the step of distilling the mixture comprises a plurality of consecutive distillation steps, and wherein the first portion of said extracted PRC enriched overhead is recycled to a stream associated with the second or later step of said distillation steps.

26. The process of claim 24, further comprising the step of adding dimethyl ether to at least one stream selected from the group consisting of said mixture, said PRC enriched overhead, and streams associated with said distillation.

27. The process of claim 24, wherein said second overhead comprises dimethyl ether in an amount effective to reduce the solubility of methyl iodide in said aqueous stream.

28. The process of claim 24, further comprising the step of providing said mixture by separating a liquid composition into a light phase and a heavy phase, said liquid composition comprising water, acetic acid, methyl iodide, methyl acetate, methanol, at least one $C_{2-12}$ alkyl iodide and said at least one PRC, wherein the light phase comprises said mixture and the heavy phase comprises methyl iodide.

29. The process of claim 28, further comprising the steps of: performing a liquid-vapor phase separation on the effluent of a methanol carbonylation reactor to form a vapor phase and a liquid phase; distilling the vapor phase to form a first overhead and a liquid product; and condensing at least a portion of the first overhead to provide said liquid composition.

30. The process of claim 29, wherein said at least one PRC comprises acetaldehyde.

31. The process of claim 30, wherein a sufficient quantity of said acetaldehyde is removed from said volatile phase to maintain a concentration of less than about 400 parts per million by weight of propionic acid in said purified acetic acid product.

32. The process of claim 30, wherein a sufficient quantity of said acetaldehyde is removed from said volatile phase to maintain a concentration of less than about 250 parts per million by weight of propionic acid in said purified acetic acid product.

33. The process of claim 29, further comprising recycling at least a portion of the extracted PRC enriched overhead directly or indirectly to the carbonylation reactor.

34. The process of claim 33, further comprising the step of adding dimethyl ether to the PRC enriched overhead.

35. The process of claim 33, further comprising forming dimethyl ether during the distillation of said mixture and reacting at least a portion of the dimethyl ether with carbon monoxide in the reactor.

36. The process of claim 35, further comprising the step of adding water to the mixture, to a stream associated with the distillation of the mixture, or into the first portion of the extracted PRC enriched overhead to promote formation of dimethyl ether during the distillation.

* * * * *